United States Patent [19]

Bassi et al.

[11] Patent Number: 5,610,277
[45] Date of Patent: Mar. 11, 1997

[54] ALCOHOL-FREE WET EXTRACTION OF GLUTEN DOUGH INTO GLIADIN AND GLUTENIN

[75] Inventors: Sukh Bassi, Atchison, Kans.; Clodualdo C. Maningat, Platte City, Mo.; Rangaswamy Chinnaswamy, Kansas City, Mo.; Darren R. Gray, St. Joseph, Mo.; Li Nie, Kansas City, Mo.

[73] Assignee: Midwest Grain Products, Atchinson, Kans.

[21] Appl. No.: 526,078

[22] Filed: Sep. 11, 1995

[51] Int. Cl.$^6$ .............................. C07K 1/30; C07K 2/00; C07K 14/415

[52] U.S. Cl. .................. 530/374; 530/375; 530/419; 530/420

[58] Field of Search .................. 530/374, 375, 530/419, 420

[56] References Cited

U.S. PATENT DOCUMENTS

| | | | |
|---|---|---|---|
| 2,309,113 | 1/1943 | Huppert | 530/378 |
| 2,861,061 | 11/1958 | Borel et al. | 530/374 |
| 2,861,062 | 11/1958 | Borel et al. | 530/374 |
| 3,615,715 | 10/1971 | Mullen | 426/138 |
| 4,645,831 | 2/1987 | Lawhon | 530/374 |
| 4,935,257 | 6/1990 | Yajima | 426/72 |
| 5,274,079 | 12/1993 | Katayama et al. | 530/372 |

FOREIGN PATENT DOCUMENTS

| | | |
|---|---|---|
| 24064 | 7/1971 | Japan . |
| 9414886 | 7/1994 | WIPO . |

OTHER PUBLICATIONS

Chemical Abstracts 123: 110534t (1995).
Sing et al. Use of Sonication and Size–Exclusion . . . Cereal Chemistry, 1990, vol. 67, No. 2, pp. 150–161.
Goforth et al, Separation of Glutenin from Gliadin . . . Cereal Chemistry, 1976, vol. 53, No. 4, pp. 608–612.
Curioni et al. Preparative isoelectric Focussing . . . Electrophoresis, 1990, vol. 11, pp. 462–467.
Gennadios et al.; Modification of Physical and Barrier Properties of Edible Wheat Gluten–Based Films; Cereal Chem. 70(4): 426–429 (1993).
Meester; Extraction et utilisation de la gliadine et de la glutenine due froment; Jan. 1974; Industries Alimentaires et Agricoles 91 Annee (1974).
Goforth et al.; Separation of Glutenin from Gliadin by Ultracentrifugation; Cereal Chem.; 53 (4) 608–612 (1976)(abstract only).
Gennadios et al.; Moisture Absorption by Grain Protein Films; Transactions of the ASAE; vol. 37(2):535–539 (1994).
Chem. Ab No. 121:257510z; Kawaguchi et al.; Gluten sheets and manufacture thereof and cleaning tools using the same for dust pickup on contact (1994).
Chem Ab No. 121:156095n; Gennadios et al.; Water vapor permeability of wheat gluten and soy protein isolate films (1994).
Chem. Ab. No. 120:219267x; Yashi et al.; Development of biodegradable gluten plastics (1994).
Chem Ab No. 119:182230f; Makoto; Biodegradable plastics derived from poly(amino acids) (1993).
Chem Ab No. 119:74215w; Domae et al.; Gluten moldings and their manufacture (1993).
Chem Ab. No. 117:9072s; Domae et al.; Biodegradable plastics containing gluten (1992).
Chem Ab. No. 116:256890h; Yamashita; Development trends on biodegradable plastics (1992).
Sato; Proteins of the soy bean and their industrial application; Chemical Abstracts 14:3299 (1920).
Sato; Proteins of the soy bean and their industrial application; Chemical Abstracts 15:1193–1194 (1921).
Davies et al.; Plasticisation and Mechanical Properties of Heat–Set Wheat Gluten; International Workshop on Gluten Proteins (1990), pp. 21–28.
Chem Ab No. 121:281872q; Hasegawa et al.; Biodegradable thermoplastic composition from corn gluten meal and its preparation (1994).
Gennadios et al.; Edible Films and Coatings from Soymilk and Soy Protein; Cereal Foods World; Dec. 1991; vol. 36, No. 12.
Yasui et al.; Development of biodegradable gluten plastic; Kobunshi Kako 1991, 40(8), 407–11.
Tolstoguzov; Thermoplastic Extrusion—The Mechanism of the Formation of Extrudate Structure and Properties; JAOCS, vol. 70, No. 4 (Apr. 1993), pp. 417–424.
Prudencio–Ferreira et al.; Protein–Protein Interactions in the Extrusion of Soya at Various TEmperatures and Moisture Contents; J. Food Science, vol. 58, No. 2 (1993) 378–381.
Paetau et al.; Biodegradable Plastic Made from Soybean Products. 1. Effect of Preparation and Processing on Mechanical Properties and Water Absorpotion; Ind. Eng. Chem. Res. 1994, 33, 1821–1827.
De Deken et al.; Wheat gluten. II. Action of reducing agents; Biochim. et Biophs. Acta 16, 566–9(1955).
Matsumoto; Breadmaking, XII. The mechanism of NaHSO$_3$ effect on gluten; J. Fermentation Technol. 33, 235–7 (1955).
Wada et al.; Studies on the production of artificial plastic masses from soybean protein; Choral Abstracts 34:2095–9(1940).

(List continued on next page.)

*Primary Examiner*—Jeffrey E. Russel
*Attorney, Agent, or Firm*—Hovey, Williams, Timmons & Collins

[57] ABSTRACT

An improved alcohol-free method for fractionating gluten into gliadin and glutenin fractions is provided where an acidic dispersion of gluten is formed with a reducing agent (e.g., sodium metabisulfite) operable for breaking disulfide bonds in the gluten protein. Thereafter, the pH of the dispersion is raised to cause glutenin to precipitate while leaving gliadin suspended in the dispersion. The respective fractions can then be separated by decanting or centrifugation. In preferred processing, the dispersion is reacidified prior to separation in order to achieve a higher degree of separation of the glutenin and gliadin.

16 Claims, No Drawings

OTHER PUBLICATIONS

Chem Ab No. 122:316010g; Kubota et al.; Biodegradable plastics obtained from water–in–soluble corn proteins; (1995).

Chem Ab. No. 122;263837y; Gontard; Edible wheat gluten films: optimization of the main process variables and improvement of water vapor barrier properties by combining gluten proteins with lipids (1995).

Chem Ab. No. 122:135036z; Nishiyama et al.; Investigation on research for degradable plastics (1995).

Chem Abs Nos. 122:29919e–29926e; 17–Food, Feed Chem.; vol. 122, 1995.

Chem Ab No. 119:265990e; Ando; Biodegradable protein products for use as packaging material or container (1993).

Chem Ab. No. 119:119103b; Nagai et al.; Biodecomposable thermoplastic moldings and their manufacture (1993).

Chem Ab. no. 19008d; Anker et al.; Shaped articles by extruding nonthermally coagulable simple proteins (1971).

Cherian et al.; Thermomechanical Behavior of Wheat Gluten Films; Effect of Sucrose, Glycerin and Sorbitol; 2 Cereal Chem.; vol. 72, No. 1, 1995. pp. 1–6.

Park et al.; Water Vapor Permeability and Mechanical Properties of grain Protein–Based Films as Affected by Mixtures of Polyethylene Glycol and Glycerin Plasticizers; Transactions of the ASAE; vol. 37(4): 1281–1285 (1994).

ALCOHOL-FREE WET EXTRACTION OF GLUTEN DOUGH INTO GLIADIN AND GLUTENIN

BACKGROUND OF THE INVENTION

1. Field of the Invention

The present invention is broadly concerned with an improved method for the fractionation of gluten to yield gliadin and glutenin. More particularly, the invention pertains to such a fractionation method which is preferably essentially free of alcohol in order to avoid the problems of alcohol recovery and environmental pollution typical of present separation techniques. The method hereof involves initially forming a dispersion of gluten in an aqueous acidic medium in the presence of a reducing agent (e.g., sodium metabisulfite) operable to break disulfide bonds in the gluten protein, followed by elevating the pH of the dispersion and causing precipitation of glutenin leaving gliadin suspended in the dispersion; the glutenin and gliadin fractions can then be separated. Use of reducing agents in the gluten dispersion lowers the viscosity of the dispersion and greatly facilitates the desired fractionation.

2. Description of the Prior Art

Wheat gluten can readily be isolated from wheat flour simply by working wheat flour dough under a stream of water. The suspendible starch fraction of the flour is washed away, leaving substantially water insoluble wheat gluten normally containing about 75% by weight protein, 8% by weight lipid, and with the remainder being ash, fiber and residual starch. Isolated wheat gluten can then be separated into its primary proteinaceous components, gliadin and glutenin.

Gliadin is a single-chained protein having an average molecular weight of about 30,000–40,000, with an isoelectric of pH 4.0–5.0. Gliadin proteins are extremely sticky when hydrated and have little or no resistance to extension. Gliadin is responsible for giving gluten dough its characteristic cohesiveness. Glutenin is a larger, multi-chained protein with an average molecular weight of about 3,000,000 ranging from 100,000 to several million. The isoelectric pH of glutenin is about 6.5–7.0. Glutenin is resistant to extension and is responsible for the elasticity of gluten dough.

Gliadin and glutenin are premium products, when available. Gliadin is known to improve the freeze-thaw stability of frozen dough and also improves microwave stability. This product is also used as an all-natural chewing gum base replacer, a pharmaceutical binder, and improves the texture and mouth feel of pasta products and has been found to improve cosmetic products. Glutenin has been used as a dough strengthening agent for bakery products and has shown potential in meat replacement products.

Generally, wheat gluten is fractionated into gliadin and glutenin proteins by initially solubilizing the gluten in dilute acid and then adding ethanol until a 70% solution is achieved. The solution is then neutralized with base and left to stand overnight at refrigeration temperatures. The ethanol-soluble gliadins go into solution while the glutenins precipitate out. Final separation involves decantation or centrifugation to yield the separate proteinaceous fractions. Although alcohol methods of the type described are effective for fractionating gliadin and glutenin in laboratory situations, these techniques are not practical for high volume, commercial manufacturing. Specifically, use of the high concentrations of ethanol can be dangerous owing to potential explosion hazards, and moreover may present an environmental hazard. Attempts at using lower concentrations of ethanol, while seemingly an improvement, ultimately present the same problems as the conventional high alcohol concentration techniques.

There is accordingly a real and unsatisfied need in the art for an improved gluten fractionation process which will yield high grade glutenin and gliadin products without the need for ethanol as a separation solvent.

SUMMARY OF THE INVENTION

The present invention overcomes the problems outlined above, and provides a gluten fractionation method for the economical separation of wheat gluten into glutenin and gliadin fractions. Preferably, the method of the invention is carried out without the use of alcohol (i.e., the gluten is dispersed and separated in a medium essentially free of alcohol and at most containing up to about 3% by weight alcohol), and involves the preparation of an acidic gluten dispersion in the presence of a reducing agent operable for breaking disulfide bonds in the gluten protein. The pH of the dispersion is then carefully adjusted so that effective separation of gliadin and glutenin can be achieved without the use of alcohol solvents.

Broadly speaking, the method of the invention involves first providing a quantity of gluten and forming a dispersion of the gluten in an aqueous acidic medium at a first acidic pH in the presence of a reducing agent, whereupon the pH of the dispersion is raised to a second level above the first pH level for causing the glutenin to precipitate from the dispersion while leaving gliadin in solution therein. Thereupon, the glutenin and gliadin are separated into respective fractions.

In more detail, the method of the invention comprises first obtaining raw gluten dough as the initial starting material for the fractionation process. The raw gluten dough is normally obtained from wheat flour dough simply by washing the dough with copious amounts of water. Gluten protein is substantially insoluble in water and forms a viscoelastic mass. The raw gluten dough generally has a solids content of about 25–35% by weight on a dry basis. Advantageously, the raw gluten dough should be freshly formed and should not have an opportunity to rest for a long period of time (i.e., more than 12 hours) before the fractionation process is commenced.

The raw wheat gluten dough should be dispersed in an aqueous acidic medium in the presence of a reducing agent, the latter serving to break disulfide bonds in the gluten protein. Generally speaking, the total solids content of the initial dispersion should be from about 8–14% by weight, more preferably from about 10–11% by weight, dry basis. In forming the dispersion, cool water is preferably used, preferably having an initial temperature of 15°–25° C., most preferably about 18°–20° C. A wide variety of acids can be used in the formation of the starting dispersion. Preferably food grade acids are used, and acids selected from the group consisting of acetic, lactic, citric, malic, succinic, phosphoric, formic, fumaric, tartaric, hydrochloric and sulfuric acids and mixtures thereof find particular utility in the invention. Similarly, a number of reducing agents can be used in the initial dispersion, so long as they have the capacity to break the disulfide bonds of gluten protein. The most preferred reducing agents are selected from the group consisting of sodium sulfite, sodium bisulfite, sodium metabisulfite and mixtures thereof. Ascorbic acid acts as both an acid and a reducing agent; however, it tends to discolor the final products of gliadin and glutenin.

The starting dispersion is normally prepared by first mixing together the water, acid and reducing agent with preliminary mixing, followed by addition of the gluten dough, which is usually done stepwise. The total time required for dispersion of the gluten should be from about 2–30 minutes, more preferably from about 5–10 minutes. As indicated, the pH level of the starting dispersion is carefully controlled. The initial pH of the dispersion is normally from about 3.5–4.5, more preferably from about 3.8–4.3. The amount of reducing agent used is dependent upon the ability of the selected agent to cleave disulfide bonds. Broadly, the reducing agent is normally used at a level of from about 0.05–0.2% by weight, and more preferably from about 0.1–0.15% by weight.

After the initial dispersion is formed, the pH is raised to a second level above the first pH level in order to cause the glutenin to precipitate from the dispersion while leaving gliadin in solution therein. An aqueous base such as ammonia is generally added to the starting dispersion to effect this pH elevation. The second pH level should preferably be from about 3.6–5.0, and more preferably from about 4.3–4.5.

In many cases, it is desirable to reacidify the dispersion in order to lower the pH and thus solubilize any remainder of gliadin in the predominantly glutenin precipitate. Again, the acids described above can be used for this purpose. Such reacidification is generally carried out to achieve a final pH of about 3.5–4.3.

In the final step of the process, the precipitated and supernatant fractions are separated, typically by settling or centrifugation. For example, the pH-adjusted dispersions can be allowed to sit at refrigeration temperatures. (4° C.) for about 16–24 hours, whereupon the gliadin layer can be decanted from the precipitated glutenin mass. Alternately, centrifugation can be carried at 5000–8000 rpm for 5–10 minutes in order to effect the fractionation. In either technique, fat and excess starch is collected with the precipitated glutenin layer. Once separated, the glutenin layer is normally washed with a 3–5% salt solution, such as soda ash, in order to allow the glutenin proteins to reagglomerate and to remove the excess starch. The glutenin fraction can then be dried by any suitable method such as convection, spray or flash drying. The liquid gliadin fraction is preferably also dried by any suitable means.

The following table sets forth a typical proximate analysis for the gluten fractions obtained using the techniques of the invention.

| Test | Gliadin | Glutenin |
| --- | --- | --- |
| % Moisture, Oven | 5–7 | 5–7 |
| % Protein, Leco (N 5.7) | 75 min. | 75 min. |
| % Fat (Acid Hydrolysis) | 2–4 | 5–9 |
| % Starch, Enzymatic Hydrolysis | 2–4 | 4–9 |
| % Ash | 2–4 | 2–4 |

The dried gliadin fraction appears to be almost white while the glutenin fraction is golden brown to tan in color. The protein content in the glutenin is slightly lower; however, the percent of protein can be increased by improved washing to remove some of the starch.

The use of reducing agent in accordance with the invention yields a number of advantages. First, the reducing agent increases the speed of dispersion and effectively lowers the viscosity of the starting dispersion in the initial step of the process. In prior attempts of dispersing gluten in the presence only of an acid, a high agitation blender is required to break down the gluten. This in turn tends to form a high viscosity dispersion, which, in combination with the solids content thereof, tends to generate heat and increase the temperature of the dispersion. The increase in dispersion temperature makes separation of the glutenin and gliadin fractions difficult if not impossible. However, by using a reducing agent, this potential problem is eliminated.

Second, the presence of reducing agent is important during addition of base to elevate the pH of the dispersion. Without a reducing agent, base addition can cause the formation of a thick mass which again can lead to undesirable temperature rises as a consequence of further mixing. Thus, the reducing agent is an important factor in maintaining relatively low dispersion temperatures, which makes fractionation of the gluten a practical process. Preferably, the maximum temperature of the dispersion prior to the drying step should be no more than about 30° C.

DESCRIPTION OF THE PREFERRED EMBODIMENT

The following examples set forth preferred fractionation techniques in accordance with the present invention. It is to be understood, however, that these examples are provided by way of illustration only and nothing therein should be taken as a limitation upon the overall scope of the invention.

EXAMPLE 1

In this laboratory scale example, wheat gluten was fractionated to yield gliadin and glutenin. In the first step of the process, one liter of city water (20° C.) was placed in a 4000 ml beaker. A conventional homogenizer-mixer (Greerco) was placed in the water, with the cutting head submerged and at least 1 inch from the bottom of the beaker, and with the deflector plate adjusted to the top of the water level. 5.8 ml of glacial acetic acid and 0.2 g sodium metabisulfite was then added to the water and the homogenizer-mixer was turned on for 5 minutes.

In the next step, 500 g of wet gluten dough (30–32% by weight solids) was added in small pieces to the beaker while the homogenizer-mixer was operating, with each gluten piece being approximately 20–30 g in size. Mixing was continued until no solid pieces were observed. At this point, the pH of the mixture was about 3.8–4.2. Thereafter, 6 ml of 5% ammonia was added to the mixture which caused it to momentarily thicken and then thin out. The pH of the mixture was about 4.3–4.5, causing the glutenin and some of the gliadin to precipitate, with a fraction of the gliadin remaining in the liquid phase. The mixture then further was agitated with the homogenizer-mixer for a period of 2–3 minutes.

Next, a second sample of the liquid fraction was centrifuged at 3000 rpm for 2 minutes, and a yellowish opaque liquid (gliadin) was observed above a thick precipitated mass (glutenin) in the bottom of the centrifuge tube. The solids content of the liquid fraction was about 2–3% by weight.

Glacial acetic acid was then added to the mixture to adjust the pH to about 4.0, in order to lower the pH from the isoelectric point of gliadin and to thereby solubilize the rest of the gliadin from the precipitate. The homogenizermixer was then operated for 2–3 minutes after acid addition.

Another sample of the liquid fraction was centrifuged as described above and exhibited two layers; the solids fraction of the liquid gliadin layer was about 4–5% by weight. At this point, the entire remainder of the sample was centrifuged at 8000 rpm for 5 minutes (Marathon 21K centrifuge, Fischer Scientific) using 85 ml tubes. The fractionated samples resulting from the centrifugation were placed in respective drying pans and dried in an oven at 35° C. for 24–48 hours. The resulting dried samples were then ground into fine gliadin and glutenin powders. In this example, approximately 75–90% by weight of the total gliadin content was recovered.

EXAMPLE 2

In this production scale example, 1,670 pounds of gluten dough (30–32% by weight solids) was placed in a scale tank. 380 gallons of city water (15°–25° C.) was added to a dispersion tank along with 8.78 liters of glacial acetic acid and 295 g of sodium metabisulfite. The mixture in the dispersion tank was agitated for 5 minutes. The gluten dough from the scale tank was then added to the dispersion tank with mixing until the dough was completely dispersed. The dispersion had a pH of about 3.8–4.2.

9.09 liters of 5% ammonia was then added to the dispersion tank with mixing for 2–3 minutes, causing the glutenin to precipitate. A small sample of the dispersion was taken and the pH was recorded (4.3–4.5). The sample was then centrifuged at 3000 rpm for 2 minutes and exhibited a precipitated mass in the bottom (glutenin) and an opaque liquid on top (gliadin). The liquid had a solids content of about 2–3% by weight. The agitator of the dispersion tank was then activated and additional glacial acetic acid was added until the pH was adjusted to about 4.0. Mixing was continued for an additional 2–3 minutes.

A second sample of the dispersion was taken and centrifuged, giving a solids content in the liquid gliadin layer of around 4–5% by weight.

The entire dispersion was then transferred to a holding tank and passed through a continuous Westphalia separator at a flow rate of 7–8 gallons per minute in order to separate the gliadin and glutenin fractions. The gliadin fraction was collected in a holding tank and then either directly spray dried or concentrated by filtration to increase the solids content to about 12–15% by weight followed by spray drying. The intermediate filtration step facilitated spray drying and removes more of the acetic acid, giving a more neutral end product. The glutenin fraction was sent to an agglomeration tank where it was combined with water and soda ash to transform the glutenin into a thick mass. The mass was then pressed to remove excess water and starch (to a solids content of about 35–40% by weight) followed by flash drying and grinding using a hammermill. Approximately 75–90% by weight of the total gliadin content was recovered.

EXAMPLE 3

In this laboratory example, lactic acid was used in lieu of acetic acid, with sodium metabisulfite as the reducing agent. The procedure followed was that described in Example 1.

EXAMPLE 4

In another production scale example, lactic acid and sodium metabisulfite were used as the acidifying and reducing agents respectively. The procedure used was the same as that set forth in Example 2.

We claim:

1. A method of fractionating wheat gluten comprising the steps of:

providing a quantity of wheat gluten;

forming a dispersion of said gluten in an aqueous acidic medium at a first acidic pH level in the presence of a reducing agent operable for breaking disulfide bonds in the gluten protein;

raising the pH of said dispersion to a second level above said first acidic pH level for causing glutenin to precipitate from the dispersion while leaving gliadin suspended in the dispersion; and separating glutenin and gliadin into respective fractions.

2. The method of claim 1, said gluten having a solids content of from about 25–35% by weight on a dry basis.

3. The method of claim 1, including the step of forming said dispersion using water having an initial temperature of about 15°–23° C.

4. The method of claim 1, including the step of forming said dispersion using an acid selected from the group consisting of acetic, lactic, citric, malic, succinic, phosphoric, formic, fumaric, tartaric, hydrochloric and sulfuric acids and mixtures thereof.

5. The method of claim 1, said first pH being from about 3.5–4.5

6. The method of claim 1, said first pH being from about 3.8–4.3.

7. The method of claim 1, said reducing agent being selected from the group consisting of sodium sulfite, sodium bisulfite, sodium metabisulfite and mixtures thereof.

8. The method of claim 1, said reducing agent being present in said dispersion at a level of from about 0.05–0.20% by weight.

9. The method of claim 1, said second pH being from about 3.6–5.0.

10. The method of claim 8, said second pH level from about 4.3–4.5.

11. The method of claim 1, including the step of, prior to said separation step, lowering the pH of said dispersion from said second pH to a third pH lower than said second level.

12. The method of claim 11, said third pH being from about 3.5–4.3.

13. The method of claim 1, said separation step comprising the steps of centrifuging said dispersion to yield a precipitated fraction and a supernatant fraction, and separately drying the precipitated fraction and supernatant fraction.

14. The method of claim 13, including the step of filtering the supernatant fraction and then spray drying the filtrate.

15. The method of claim 13, including the step of pressing the precipitated fraction to remove moisture therefrom and then flash drying the pressed precipitated fraction.

16. The method of claim 1, said dispersion being essentially free of alcohol.

* * * * *